United States Patent

Krüger et al.

Patent Number: 5,237,086
Date of Patent: Aug. 17, 1993

[54] FUNGICIDAL DERIVATIVES OF CARBOCYCLIC ANILIDES

[75] Inventors: Bernd-Wieland Krüger; Klaus Sasse, both of Bergisch-Gladbach; Wilhelm Brandes, Leichlingen, all of Fed. Rep. of Germany

[73] Assignee: Bayer Aktiengesellschaft, Leverkusen, Fed. Rep. of Germany

[21] Appl. No.: 931,178

[22] Filed: Aug. 17, 1992

Related U.S. Application Data

[62] Division of Ser. No. 568,454, Aug. 15, 1990, Pat. No. 5,166,392.

[30] Foreign Application Priority Data

Sep. 2, 1989 [DE] Fed. Rep. of Germany ........ 3929231
Apr. 21, 1990 [DE] Fed. Rep. of Germany ........ 4012712

[51] Int. Cl.$^5$ .................. C07C 43/00; C07C 69/00
[52] U.S. Cl. .................................. 558/271; 558/272
[58] Field of Search .................. 558/271, 272; 524/91; 514/476, 579; 562/493, 456

[56] References Cited

U.S. PATENT DOCUMENTS

| | | | |
|---|---|---|---|
| 4,812,498 | 3/1989 | Nakahara et al. | 524/91 |
| 4,816,504 | 3/1989 | Bailey et al. | 524/91 |
| 4,990,661 | 2/1991 | Petersen et al. | 562/493 |
| 4,990,663 | 2/1991 | Chang et al. | 562/456 X |

FOREIGN PATENT DOCUMENTS

| | | |
|---|---|---|
| 0100615 | 2/1984 | European Pat. Off. |
| 0125901 | 11/1984 | European Pat. Off. |
| 0247480 | 12/1987 | European Pat. Off. |
| 0293718 | 12/1988 | European Pat. Off. |
| 2018783 | 11/1970 | Fed. Rep. of Germany |
| 3832396 | 2/1990 | Fed. Rep. of Germany |
| 1588718 | 4/1970 | France |

Primary Examiner—Arthur C. Prescott
Attorney, Agent, or Firm—Sprung Horn Kramer & Woods

[57] ABSTRACT

Fungicidal derivatives of carboxyclic anilides of the formula

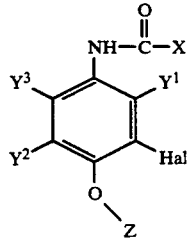

(I)

in which
X represents optionally alkyl-substituted cycloalkyl or optionally alkyl-substituted cycloalkenyl,
Hal represents halogen, and
$Y^1$, $Y^2$ and $Y^3$ independently of one another represent hydrogen, halogen, optionally halogen-substituted alkyl, optionally halogen-substituted alkoxy or optionally halogen-substituted alkylthio, and
Z represents the groups $COOR^2$ or $COR^1$, where
$R^1$ and $R^2$ are identical or different and represent optionally halogen-substituted alkyl, alkenyl, alkoxyalkyl, alkylthioalkyl, polyalkoxyalkyl and optionally substituted cycloalkyl, optionally substituted phenyl, optionally substituted phenylalkyl or substituted phenoxyalkyl.

7 Claims, No Drawings

FUNGICIDAL DERIVATIVES OF CARBOCYCLIC ANILIDES

This is a division of application Ser. No. 568,454, filed Aug. 15, 1990, now U.S. Pat. No. 5,166,392.

The present invention relates to new cycloalkyl- or cycloalkenylcarboxanilides, to a process for their preparation, and to their use for combating pests, in particular fungi.

It is known that certain carbamates have good fungicidal properties (cf. EP 293,718).

Furthermore, many carboxanilides having a fungicidal action are known, in particular those having a powerful action against benzimidazole-tolerant plant pathogens (cf. EP 117,024, EP 125,901, EP 100,615).

New cycloalkyl or cycloalkenyl-carboxanilides of the general formula (I)

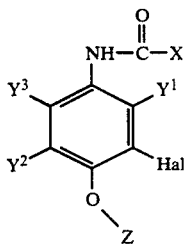

in which
X represents optionally alkyl-substituted cycloalkyl or optionally alkyl-substituted cycloalkenyl,
Hal represents halogen, and
$Y^1$, $Y^2$ and $Y^3$ independently of one another represent hydrogen, halogen, optionally halogen-substituted alkyl, optionally halogen-substituted alkoxy or optionally halogen-substituted alkylthio, and
Z represents the groups $COOR^2$ or $COR^1$, where
$R^1$ and $R^2$ are identical or different and represent optionally halogen-substituted alkyl, alkenyl, alkoxyalkyl, alkylthioalkyl, polyalkoxyalkyl and optionally substituted cycloalkyl, optionally substituted phenyl, optionally substituted phenylalkyl or substituted phenoxyalkyl,
have been found.

The substituted cycloalkyl- or cycloalkenyl-carboxanilides of the formula (I) contain one or more centers of asymmetry and can therefore be in the form of diastereomers or mixtures of diastereomers, obtained in varying ratios. They are mainly obtained in the form of racemates.

Furthermore, it has been found that the new substituted cycloalkyl- or cycloalkenylcarboxanilides of the formula (I)

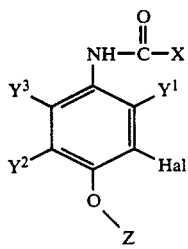

in which
X is optionally alkyl-substituted cycloalkyl or optionally alkyl-substituted cycloalkenyl,
Hal is halogen and
$Y^1$, $Y^2$ and $Y^3$ are identical or different and represent hydrogen, halogen, optionally halogen-substituted alkyl, optionally halogen-substituted alkoxy or optionally halogen-substituted alkylthio, and
Z represents the groups $COOR^2$ or $COR^1$, where
$R^1$ and $R^2$ are identical or different and represent optionally halogen-substituted alkyl, alkenyl, alkoxyalkyl, alkylthioalkyl, polyalkoxyalkyl and optionally substituted cycloalkyl, optionally substituted phenyl, optionally substituted phenylalkyl or substituted phenoxyalkyl,
are obtained when aminophenols of the formula (II)

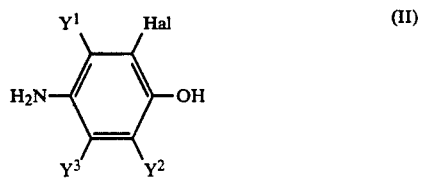

in which
Hal, $Y^1$, $Y^2$ and $Y^3$ have the abovementioned meanings, are reacted, in a first reaction step, with carboxylic acid derivatives of the formula (III)

in which
X has the abovementioned meaning and
$Hal^1$ represents halogen, preferably chlorine, or represents a leaving group customary in acylation reactions, preferably an activating ester radical,
if appropriate in the presence of an acid acceptor and if appropriate in the presence of a solvent or diluent, and these resulting intermediates of the formula (IV)

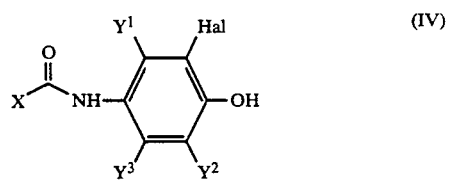

in which
X, $Y^1$, $Y^2$, $Y^3$ and Hal have the abovementioned meanings, are reacted in a second step with carbonyl derivatives of the formula (V)

in which
Z has the abovementioned meaning and
$Hal^2$ represents halogen, preferably chlorine, or a leaving group customary in acylation reactions, preferably an activating ester radical,
if appropriate in the presence of an acid acceptor and if appropriate in the presence of a solvent or diluent.

Finally, it has been found that the substituted cycloalkyl- or cycloalkenyl-carboxanilides of the formula (I) and (IVa) have, inter alia, a powerful fungicidal activity. The new compounds can also be used with other known, highly-effective compounds in synergistic mixtures.

Within the scope of the present invention, the substituents preferably have the following meanings:

Unless stated otherwise, halogen can denote fluorine, chlorine, bromine and iodine, preferably fluorine, chlorine and bromine.

Alkyl, alkoxy and alkylthio represent radicals which have 1-8, preferably 1-6 and particularly preferably 1-4 carbon atoms per alkyl unit, for example methyl, ethyl, n- and iso-propyl, n-, sec-, iso- and tert.-butyl, pentyl, n-hexyl or iso-hexyl, methoxy, ethoxy, n- and iso-propoxy, n-, sec-, iso- and tert.-butoxy, pentoxy and hexoxy, methylthio, ethylthio, n- and iso-propylthio, n-, sec.-, iso- and tert.-butylthio, pentylthio and hexylthio.

Halogenoalkoxy or halogenoalkylthio generally represents a straight-chain or branched hydrocarbon radical which has 1-6 carbon atoms and 1-9 identical or different halogen atoms and which is bonded via oxygen, or sulphur, respectively. Preferred radicals are those having 1-4 carbon atoms and 1-5 identical or different halogen atoms. Very particularly preferred radicals are those having 1 or 2 carbon atoms and 1-3 identical or different halogen atoms. The following may be mentioned as examples: trifluoromethoxy, trichloromethoxy, difluorochloromethoxy, dichlorofluoromethoxy, difluoroethoxy, trifluoroethoxy, tetrafluoroethoxy, pentafluoroethoxy, trifluoromethylthio, trichloromethylthio, difluorochloromethylthio, dichlorofluoromethylthio, difluoroethylthio, trifluoromethylthio and tetrafluoroethylthio.

Halogenoalkyl has the meaning of halogenoalkoxy, with the difference that the oxygen is missing.

Cycloalkyl generally represents a cyclic hydrocarbon radical having 3-10 carbon atoms. Radicals having 3-7 carbon atoms are preferred. The following may be mentioned as examples: cyclopropyl, cyclobutyl, cyclopentyl, cyclohexyl, cycloheptyl and cyclodecanyl.

The cycloalkyl radicals can be monosubstituted to polysubstituted. Substituents which may be mentioned are alkyl having 1-4 carbon atoms, halogen, halogenoalkyl having 1 to 4 carbon atoms and 1 to 9 identical or different halogen atoms, alkoxy having 1 to 4 carbon atoms, hydroxyl and alkylcarbonyloxy having 1 to 6 carbon atoms in the alkyl moiety.

Cycloalkenyl generally represents a cyclic hydrocarbon radical having 5-10 carbon atoms.

Radicals having 5-7 carbon atoms are preferred. The following may be mentioned as examples: cyclopentenyl, cyclohexenyl and cycloheptenyl.

The cycloalkenyl radicals can be monosubstituted to polysubstituted. Substituents which may be mentioned are alkyl radicals having 1-6 carbon atoms.

In this context, the preferred and particularly preferred meanings of alkyl are those which have already been given further above.

Phenyl, phenylalkyl and substituted phenoxyalkyl generally represents phenyl, phenylalkyl and phenoxyalkyl, in which phenyl hydrogen atoms are optionally replaced by one or more substituents $Y^{1'}-Y^{5'}$. In this context, $Y^{1'}-Y^{5'}$ have the meaning of $Y^1$, $Y^2$ and $Y^3$ as well as nitro and cyano.

Alkenyl generally represents a straight-chain or branched hydrocarbon radical having 2 to 8 carbon atoms and one or more, preferably one or two, double bonds. Lower alkenyl having 2 to 6 carbon atoms and one double bond is preferred. An alkenyl radical having 2 to 5 carbon atoms and one double bond is particularly preferred.

Formula (I) provides a general definition of the substituted cycloalkyl- or cycloalkenyl-carboxanilides according to the invention. Preferred compounds of the formula (I) are those where represents cyclopropyl, cyclobutyl, cyclopentyl, cyclohexyl or cycloheptyl, each of which is optionally monosubstituted to tetrasubstituted by identical or different substituents from the series comprising straight-chain or branched alkyl radicals having 1-4 carbon atoms, or represents cycloalkenyl having 5-7 ring members are optionally monosubstituted to hexasubstituted by identical or different substituents from the series comprising straight-chain or branched alkyl radicals having 1-4 carbon atoms, Hal represents fluorine, chlorine or bromine, $Y^1$, $Y^2$ and $Y^3$ are identical or different and represent hydrogen, fluorine, chlorine, bromine, straight-chain or branched alkyl having 1-4 carbon atoms, straight-chain or branched alkoxy or alkylthio each having 1-4 carbon atoms, or represent halogenoalkyl, halogenoalkoxy or halogenoalkylthio each having 1-4 carbon atoms in the straight-chain or branched alkyl moiety and having 1-5 identical or different halogen atoms.

represents $COOR^2$ or $COR^1$, where $R^1$ and $R^2$ are identical or different and represent $C_1-C_8$-alkyl, $C_2-C_8$-alkenyl, $C_1-C_4$-alkoxy-$C_1-C_4$-alkyl, $C_1-C_4$-alkoxy-$C_1-C_4$-alkoxy-$C_1-C_4$-alkyl or $C_1-C_4$-alkylthio-$C_1-C_4$-alkyl, each of which is optionally mono-substituted to nonasubstituted by halogen, or represent $C_3-C_7$-cycloalkyl which is unsubstituted or monosubstituted to pentasubstituted by identical or different substituents from the series comprising $C_1-C_4$-halogenoalkyl, halogen, $C_1-C_4$-alkyl, $C_1-C_4$-alkoxy, hydroxyl and $C_1-C_6$-alkylcarbonyloxy, or represent phenyl-$C_1-C_4$-alkyl which is unsubstituted or monosubstituted to pentasubstituted in the phenyl moiety by identical or different substituents from the series comprising $Y^{1'}-Y^{5'}$, or represent phenoxyalkyl which is unsubstituted or monosubstituted to pentasubstituted in the phenyl moiety by identical or different substituents from the series comprising $Y^{1'}-Y^{5'}$, where $Y^{1'}-Y^{5'}$ have the meaning of $Y^1-Y^3$, $NO_2$ and cyano.

Particularly preferred compounds of the formula (I) are those where

X represents cyclopropyl, cyclobutyl, cyclopentyl, cyclohexyl or cycloheptyl, each of which is monosubstituted or disubstituted by identical or different substituents from the series comprising straight-chain or branched alkyl radicals having 1-4 carbon atoms, or represents cyclopentenyl, cyclohexenyl or cycloheptenyl, each of which is optionally monosubstituted or disubstituted by identical or different substituents from the series comprising straight-chain or branched alkyl radicals having 1-4 carbon atoms, $Y^1$, $Y^2$ and $Y^3$ are identical or different and represent hydrogen, fluorine, chlorine, bromine, methyl or trifluoromethyl, and Hal represents fluorine, chlorine or bromine, represents $COOR^2$ or $COR^1$, where $R^1$ and $R^2$ are identical or different and represent $C_1-C_6$-alkyl, $C_2-C_6$-alkenyl, $C_1-C_4$-alkoxy-$C_1-C_4$-alkyl, $C_1-C_4$-alkoxy-$C_1-C_4$-alkoxy-$C_1-C_4$-alkyl or $C_1-C_4$-alkylthio-$C_1-C_2$-alkyl, or represent $C_3-C_7$-cycloalkyl which is unsubstituted or monosubstituted to trisubstituted by identical or different substituents from the series comprising fluorine, chlorine, bromine, $C_1$–$C_2$-alkyl, $C_1$–$C_2$-alkoxy or $C_1$–$C_6$-alkylcarbonyloxy, or represent phenyl which is unsubstituted or monosubstituted to trisubstituted by identical or different substituents from the series comprising nitro, cyano, fluorine, chlorine, bromine, methyl, trifluoromethyl, trifluoromethylthio, methoxy and trifluoromethoxy, or represent phenyl-$C_1$–$C_2$-alkyl which is unsubstituted or monosubstituted to trisubstituted by identical or different substituents from the series comprising nitro, cyano, fluorine, chlorine, bromine, methyl, trifluoromethyl, trifluoromethylthio, methoxy and trifluoromethoxy, or represent phenoxy-$C_1$–$C_2$-alkyl which is unsubstituted or monosubstituted to trisubstituted by identical or different substituents from the series comprising nitro, cyano, fluorine, chlorine, bromine, methyl, trifluoromethyl, trifluoromethylthio, methoxy and trifluoromethoxy.

Very particularly preferred compounds of the formula (I) are those where

X represents cyclopentyl, cyclohexyl, cycloheptyl, cyclopentenyl, cyclohexenyl or cycloheptenyl, each of which is substituted in the 1- or 1,3-position by methyl or ethyl and each of which is optionally additionally substituted by a further alkyl radical having 1-3 carbon atoms, Hal represents fluorine, chlorine or bromine, and $Y^1$, $Y^2$ and $Y^3$ are identical or different and represent hydrogen, fluorine, chlorine, bromine or trifluoromethyl, Z represents $COOR^2$ or $COR^1$, where $R^1$ and $R^2$ are identical or different and represent $C_1$–$C_4$-alkyl, $C_2$–$C_5$-alkenyl, $C_1$–$C_4$-alkoxy-$C_1$–$C_4$-alkyl or $C_1$–$C_4$-alkoxy-$C_1$–$C_4$-alkoxy-$C_1$–$C_4$-alkyl, or represent $C_3$–$C_7$-cycloalkyl which is monosubstituted to trisubstituted by identical or different substituents from the series comprising methoxy, fluorine, chlorine, bromine, methyl and $C_1$–$C_4$-alkylcarbonyloxy, or represent phenyl which is monosubstituted to trisubstituted by identical or different substituents from the series comprising nitro, cyano, fluorine, chlorine, bromine, methyl and methoxy, or represent phenylmethyl which is monosubstituted to trisubstituted by identical or different substituents from the series comprising nitro, cyano, fluorine, chlorine, bromine, methyl and methoxy.

If, for example, 2,6-dichloro-4-amino-phenol, 1-methyl-1-chlorocarbonylcyclohexane and butyl chloroformate are used as starting substances, the course of the reaction can be represented by the following equation:

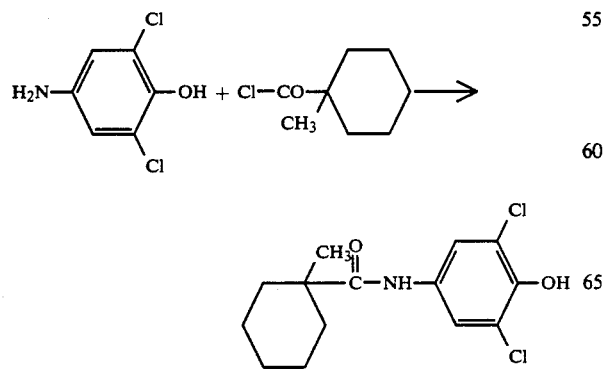

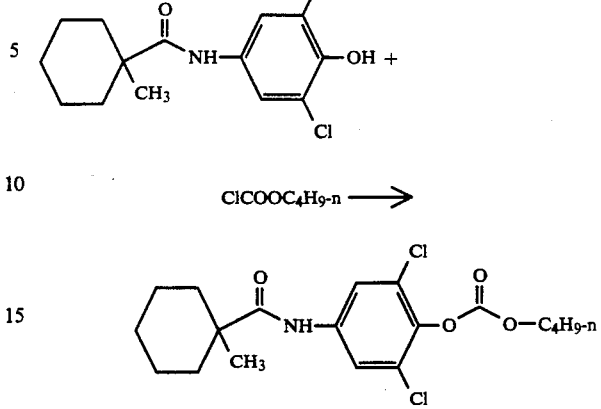

Formula (II) provides a general definition of the aminophenols required as starting substances for carrying out the process according to the invention. In this formula (II), the radicals Hal and $Y^1$–$Y^3$ have the meanings already given in connection with the description of the compounds of the formula (I) according to the invention. Most of the compounds are known and can be prepared by analogous processes (cf. "Methoden der organischen Chemie" [Methods of Organic Chemistry], Houben-Weyl, Volume VI/1c, Phenols, Part 1, Georg Thieme Verlag, Stuttgart, 1976, and "Reaktionen der organischen Synthese" [Reactions in Organic Synthesis], Cesare Ferri, p. 81, 89, 91, 97, 118, 120, 122, 124, 126, 128, Georg Thieme Verlag, Stuttgart, 1978).

The 4-amino-2-chloro- or -2-bromo-6-trifluoromethylphenols are known from Japanese Kokai Tokkyo Koho Jp 61/126055, and, for example 4-amino-2,3,5,6-tetrafluorophenol, from Zh. Org. Khim. 10(9), 1923–1927 (1974). The compounds of the formula (II A)

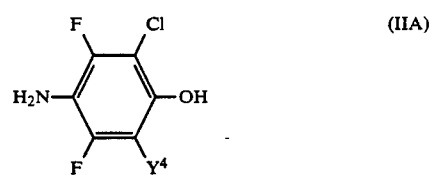

in which $Y^4$ represents fluorine or chlorine, are a subject of EP-A-293,718 and are prepared for example from corresponding hydroxybenzoic acids of the formula (V A)

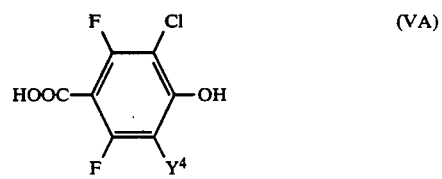

by decarboxylating to form phenols of the formula (VI A)

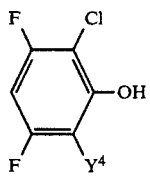

(VIA)

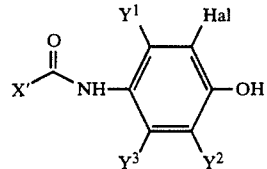

(IVa)

followed by nitration, to give the nitro compounds of the formula (VII A)

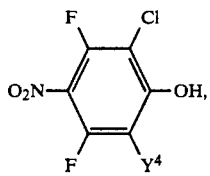

(VIIA)

which are then hydrogenated, for example using hydrogen and Raney nickel, to give the corresponding amines of the formula (II A).

The compounds of the formula (VII A) are also a subject of EP-A-293,718.

Formula (III) in which X represents cycloalkyl or cycloalkenyl provides a general definition of the cycloalkanecarboxylic acid derivatives or cycloalkenecarboxylic acid derivatives furthermore required for carrying out the process according to the invention. In this formula (III), the radicals X and $Hal^1$ have the meanings already given in connection with the description of the compounds of the formula (I) according to the invention. The compounds are known and can be prepared by analogous processes (cf. Diversi et. al., Synthesis 1971, 258; U.S. Pat. No. 3,674,831; "Reaktionen der organischen Synthese [Reactions in Organic Syntheses]", Cesare Ferri, p. 460, 461, 1978, Georg Thieme Verlag, Stuttgart); Houben-Weyl, Methoden der organischen Chemie [Methods of Organic Chemistry], Vol. E5, Pt. 1, p. 211, 320, 343, 428 et seq., G. Thieme-Verlag, Stuttgart, 1985).

The carboxylic acid derivatives and carbonic acid derivatives of the formula (V) in which Z and $Hal^2$ have the abovementioned meanings, which are furthermore required for carrying out the process according to the invention, are known and can be prepared by analogous processes (cf. "Reaktion der organischen Synthese [Reaction of Organic Synthesis]" Cesare Ferri, p. 432 et seq., 460 et seq. 1978, Georg Thieme Verlag, Stuttgart; Houben-Weyl, "Methoden der organischen Chemie [Methods of Organic Chemistry], Carbonic Acid Derivatives, Vol. E4, p. 9 et seq., Georg Thieme Verlag, Stuttgart, 1983; Vol. E5 Pt. 1, p. 193 et seq., Georg Thieme Verlag, Stuttgart, 1985).

Formula (IV) provides a general definition of the acylaminophenols used as intermediates in the process according to the invention.

New compounds from amongst the compounds of the formula (IV) are those of the formula (IVa)

in which
$X'$ represents an optionally alkyl-substituted cycloalkenyl radical, preferably a $C_1$–$C_2$-alkyl-substituted cyclopentenyl, cyclohexenyl or cycloheptenyl radical, and
$Y^1$, $Y^2$, $Y^3$ and Hal have the abovementioned meanings, The new acylamino derivatives of the formula (IVa) are obtained by reacting aminophenols of the formula (II)

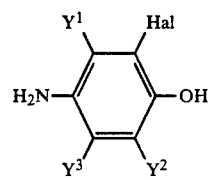

(II)

in which
$Y^1$, $Y^2$, $Y^3$ and Hal have the abovementioned meanings,
with carboxylic acid derivatives of the formula (IIIa)

(IIIa)

in which
$X'$ and $Hal^1$ have the abovementioned meanings, if appropriate in the presence of a solvent and if appropriate in the presence of an acid acceptor.

The remaining compounds of the formula (IV) can be obtained correspondingly or by known processes.

If appropriate, the process according to the invention is carried out in the presence of acid acceptors. Acid acceptors which can be used are all customary acid-binding agents. The following have proved particularly useful: alkali metal carbonates and alkali metal alcoholates, such as sodium carbonate, potassium carbonate, sodium methylate, potassium methylate, sodium ethylate or potassium ethylate, furthermore aliphatic, aromatic and heterocyclic amines, for example triethylamine, trimethylamine, dimethylaniline, 1,8-diazobicyclo-(5,4,0)-undec-7-ene, dimethylbenzylamine and pyridine.

For carrying out the process according to the invention, 1–2 moles, in particular 1–1.4 moles, of the compounds of the general formula (III), or (IIIa), are preferably employed in the first reaction step per mole of amino-phenol of the general formula (II).

In the second reaction step of the process according to the invention, it is preferred to employ 1–2 moles, in particular 1–1.4 moles, of the compounds of the general formula (V) per mole of acylaminophenol of the formula (IV) or (IVa).

Suitable diluents for carrying out the process according to the invention are virtually all inert organic diluents. These include, in particular, aliphatic and aromatic, optionally halogenated hydrocarbons, such as pentane, hexane, heptane, cyclohexane, petroleum ether, benzine, ligroin, toluene, xylene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methylpyrrolidone, and also dimethylsulphoxide, tetramethylene sulphone and hexamethylphosphoric triamide.

The process according to the invention is generally carried out at temperatures between $-50°$ C. and $120°$ C. The range between $0°$ C. and $110°$ C. is preferred. The reactions are generally carried out under atmospheric pressure.

Working up is carried out by customary methods, for example by extracting the products with toluene or methylene chloride from the reaction mixture which is diluted with water, washing the organic phase with water, drying and distilling the products, or by so-called "incipient distillation", that is to say, prolonged heating to moderately increased temperatures under reduced pressure in order to free the product from the last volatile constituents, or by chromatographic purification via silica gel, or, for example, by crystallization. The compounds are characterized by the refractive index, melting point, $R_f$ value or boiling point.

The active compounds according to the invention are suitable for use for combating pests, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Bactericidal agents are employed in plant protection for combating Pseudomonadaceae, Rhizobiaceae, Enterobacteriaceae, Corynebacteriaceae and Streptomycetaceae.

Some causative organisms of fungal and bacterial diseases which come under the generic names listed above may be mentioned as examples, but not by way of limitation:

Xanthomonas species, such as, for example, *Xanthomonas campestris pv. oryzae;*

Pseudomonas species, such as, for example, *Pseudomonas syringae pv. lachrymans;*

Erwinia species, such as, for example, *Erwinia amylovora;*

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubense;*

Plasmopara species, such as, for example, *Plasmopara viticola;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae* and

Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

In this context, the active compounds according to the invention can be employed with particularly good success for combating Botrytis fungi on beans and for combating cereal diseases, such as, for example, against Pseudocercosporella.

The active compounds are furthermore suitable for combating animal pests, preferably arthropods and nematodes, in particular insects and arachnids, encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera spec.*

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germancia, Acheta domesticus,* Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Phylloxera vastatrix,* Pemphigus spp., *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Scorpio maurus* and *Latrodectus mactans.*

From the order of the Acarina, for example Acarus siro, Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The phytoparasitic nematodes include Pratylenchus spp., *Radopholus similis, Ditylenchus dipsaci, Tylenchulus semipenetrans,* Heterodera spp., Globodera spp., Meloidogyne spp., Aphelenchoides spp., Longidorus spp., Xiphinema spp. and Trichodorus spp.

The active compounds can be converted into the customary formulations, such as solutions, emulsions, suspensions, powders, foams, pastes, granules, aerosols, very fine capsules in polymeric substances, and in coating compositions for seeds, and also ULV formulations.

These formulations are produced in a known manner, for example by mixing the active compounds with extenders, that is, liquid solvents, liquefied gases under pressure, and/or solid carriers, optionally with the use of surface-active agents, that is emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water. By liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products. As dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, and in mixtures with fertilizers and other growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02%, are required at the place of action.

EXAMPLE 1

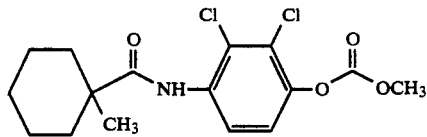

4 g (13.0 mmol) of 2,3-dichloro-4-(1-methylcyclohexyl-carbonyl)-amino-phenol are dissolved in 50 ml of tetrahydrofuran, and 2.5 ml (18.5 mmol) of triethylamine are added. 1.5 g (14.3 mmol) of methyl chloroformate are subsequently added dropwise at 20° C. to the reaction mixture. The mixture is stirred for 2 hours at 20° C., and the solvent is then distilled off under a water pump vacuum. The residue which remains is then chromatographed over silica gel (eluent: petroleum ether: acetone=8.2). Yield: 4.4 g (98% of theory). M.p.: 125° C.

The following compounds of the formula (I)

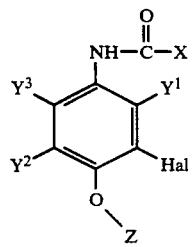

are prepared analogously:

| Example No. | X | $Y^1$ | $Y^2$ | $Y^3$ | Hal | Z | Physical data (m.p.) |
|---|---|---|---|---|---|---|---|
| 2 | 1-methylcyclohexyl | Cl | H | H | Cl | $COOCH_2CH(CH_3)_2$ | 109° C. |
| 3 | 1-methylcyclohexyl | Cl | H | H | Cl | $COOC_3H_{7n}$ | 122° C. |
| 4 | 1-methylcyclohexyl | Cl | H | H | Cl | $COOCH_2CH(CH_3)C_2H_5$ | 67° C. |
| 5 | 1-methylcyclohexyl | Cl | H | H | Cl | CO-(1-methylcyclohexyl) | 63° C. |
| 6 | 1-methylcyclohexyl | Cl | H | H | Cl | CO-(1-OCOCH$_3$-cyclopropyl) | 91° C. |

-continued

| Example No. | X | Y¹ | Y² | Y³ | Hal | Z | Physical data (m.p.) |
|---|---|---|---|---|---|---|---|
| 7 | 1-methylcyclohexyl | Cl | H | H | Cl | CO-(1-chlorocyclopropyl) | 107° C. |
| 8 | 1-methylcyclohexyl | Cl | H | H | Cl | CO-(1-methoxycyclopropyl) | 125° C. |
| 9 | 1-methylcyclohexyl | Cl | H | H | Cl | CO-(1-methylcyclopropyl) | 110° C. |
| 10 | 1-methylcyclohexyl | Cl | H | H | Cl | COCH₃ | 105° C. |
| 11 | 1-methylcyclohexyl | Cl | H | H | Cl | COC₄H₉-t | 136° C. |
| 12 | 1-methylcyclohexyl | Cl | H | H | Cl | COCH(C₂H₅)C₄H₉-n | 45° C. |
| 13 | 1-methylcyclohexyl | Cl | H | H | Cl | COCH₂-phenyl | 71° C. |
| 14 | 1-methylcyclohexyl | Cl | H | H | Cl | COCH₂-(2,4,6-trimethylphenyl) | 102° C. |
| 15 | 1-methylcyclohexyl | Cl | H | H | Cl | COCH₂-(2-methyl-4-tert-butylphenyl) | 110° C. |
| 16 | 1-methylcyclohexyl | Cl | H | H | Cl | COCH₂-(4-chlorophenyl) | 108° C. |
| 17 | 1-methylcyclohexyl | Cl | H | H | Cl | COCH₂-(4-fluoro-2-methylphenyl) | 66° C. |
| 18 | 1-methylcyclohexyl | Cl | H | H | Cl | COCH₂-(2-trifluoromethylphenyl) | 90° C. |

-continued

| Example No. | X | Y¹ | Y² | Y³ | Hal | Z | Physical data (m.p.) |
|---|---|---|---|---|---|---|---|
| 19 | 1-methylcyclohexyl | Cl | H | H | Cl | COCH₂-(2,6-dichlorophenyl) | 145° C. |
| 20 | 1-methylcyclohexyl | Cl | H | H | Cl | COCH₂-(2,3,5,6-tetramethylphenyl) | 104° C. |
| 21 | 1-methylcyclohexyl | Cl | H | H | Cl | COC(CH₃)₂-(3,4-dichlorophenyl) | 82° C. |
| 22 | 1-methylcyclohexyl | Cl | H | H | Cl | COCH₂-(3-bromo-2,4,6-trimethylphenyl) | 128° C. |
| 23 | 1-methylcyclohexyl | Cl | H | H | Cl | COCH₂-(4-methoxyphenyl) | 122° C. |
| 24 | 1-methylcyclohexyl | Cl | H | H | Cl | COCH₂-(4-tert-butyl-2,6-dimethylphenyl) | 93° C. |
| 25 | 1-methylcyclohexyl | F | F | F | Cl | CO-(1-methylcyclohexyl) | 35° C. |
| 26 | 1,3-dimethylcyclohexyl | Cl | H | H | Cl | COOCH₃ | |
| 27 | 1,2,4-trimethylcyclohexyl | Cl | H | H | Cl | COOCH₃ | |
| 28 | 1-methylcyclohex-3-enyl | Cl | H | H | Cl | COOCH₃ | |

-continued

| Example No. | X | Y¹ | Y² | Y³ | Hal | Z | Physical data (m.p.) |
|---|---|---|---|---|---|---|---|
| 29 | 1,5-dimethylcyclohexenyl | Cl | H | H | Cl | COOCH$_3$ | |
| 30 | 1-methylcyclohexyl | Cl | H | H | Cl | COO-phenyl | |
| 31 | 1-methylcyclohexyl | Cl | H | H | Cl | COOCH$_2$-phenyl | |
| 32 | 1-methylcyclohexyl | Cl | H | H | Cl | COCH$_2$O-phenyl | |
| 33 | 1-methylcyclohexyl | Cl | H | H | Cl | COCH$_2$-(2,4-dichlorophenyl) | 72° C. |
| 34 | 1-methylcyclohexyl | H | Cl | H | Cl | COOCH$_2$CH$_2$OC$_2$H$_5$ | |
| 35 | 1-methylcyclohexyl | Cl | H | H | Cl | COOCH$_2$CH$_2$OC$_2$H$_5$ | 52° C. |
| 36 | 1-methylcyclohexyl | Cl | H | H | Cl | COOCH$_2$CH$_2$OCH$_3$ | |
| 37 | 1-methylcyclohexyl | Cl | H | H | Cl | COOCH$_2$CH$_2$OC$_3$H$_7$-i | |
| 38 | 1-methylcyclohexyl | Cl | H | H | Cl | COOCH$_2$CH$_2$OC$_4$H$_9$-n | |
| 39 | 1-methylcyclohexyl | Cl | H | H | Cl | COOCH$_2$CH$_2$OCH(CH$_3$)C$_2$H$_5$ | |
| 40 | 1-methylcyclohexyl | Cl | H | H | Cl | COOCH$_2$CH$_2$OC$_3$H$_7$-n | |
| 41 | 1-methylcyclohexyl | Cl | H | H | Cl | COOCH$_2$CH(CH$_3$)OCH$_3$ | |

-continued

| Example No. | X | Y¹ | Y² | Y³ | Hal | Z | Physical data (m.p.) |
|---|---|---|---|---|---|---|---|
| 42 | cyclohexyl-CH$_3$ | Cl | H | H | Cl | COOCH$_2$CH$_2$OCH$_2$CH$_2$OC$_2$H$_5$ | $n_D^{20}$ 1.5116 |
| 43 | 1-methylcyclohexenyl | Cl | H | H | Cl | COOCH$_2$CH$_2$OC$_2$H$_5$ | |

PREPARATION EXAMPLES

Preparation of the starting compounds

Example A1

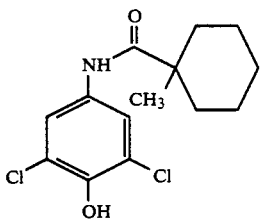

18.5 g (0.085 mol) of 4-amino-2,6-dichlorophenol are dissolved in 150 ml of tetrahydrofuran, and first 8.6 g (0.085 mol) of triethylamine and then, at 0° C. internal temperature, 15 g (0.094 mol) of 1-methylcyclohexanecarboxylic acid chloride are added. The mixture is stirred overnight at 20° C., and another 5 g of carboxylic acid chloride and 2.8 g of triethylamine are then added to the reaction mixture in order to complete the reaction. After 2 hours, the mixture is poured onto ice, and the solid which is filtered off with suction is recrystallized from toluene. The abovementioned compound of melting point 140° C. is obtained; yield: 22.3 g (=87% of theory).

The compounds of the formula (IV) and (IVa), respectively, are obtained analogously:

Example A2

3,5-Dichloro-2,6-difluoro-4-hydroxybenzoic acid 300 g of potassium hydroxide, 600 ml of water, 15 g of tetrabutylammonium chloride and 135 g of 3,5-dichloro-2,4,6-trifluorobenzotrifluoride are initially introduced into a stirred vessel, and the mixture is then refluxed for 5 hours. After the reaction has finished, the mixture is cooled and rendered acid by dropwise addition of hydrochloric acid. The solid is filtered off with suction and dried in vacuo. Yield: 93 g, having a melting point of 102°–105° C.

Example A3

3-Chloro-2,5,6-trifluoro-4-hydroxy-benzoic acid

Analogously to Example A1, 400 g of NaOH, 1,200 ml of water, 15 g of tetraethylammonium chloride and 276 g of 3-chlorotetrafluorobenzotrifluoride, refluxed for 6 hours, give 238 g of product having a melting point of 87°–90° C.

Example A4

2,6-Dichloro-3,5-difluorophenol 50 g of 3,5-dichloro-2,6-difluoro-4-hydroxybenzoic acid and 10 ml of dimethylformamide are mixed, and the mixture is heated. Carbon dioxide is evolved at 105°–130° C., and the mixture is allowed to react at this temperature until the reaction is complete. After this, 200 ml of toluene and then 80 ml of water are stirred in, the phases are separated, and the organic phase is dried and then distilled. This gives 34 g of the product having a boiling point of 87°–88° C. and a refractive index of $[n]_D^{20}$: 1.5310.

Example A5

Analogously to Example A3, 2-chloro-3,5,6-trifluorophenol is obtained, having a boiling point of 68°–70° C./20 mbar.

Example A6

2,6-Dichloro-3,5-difluoro-4-nitrophenol 20 g of 2,6-dichloro-3,5-difluorophenol are initially introduced in 70 ml of acetic acid, and 8 g of 98% strength nitric acid are added dropwise. Stirring is subsequently continued at room temperature for 2 hours, and the mixture is taken up in 150 ml of dichloromethane and washed twice with water. After the dichloromethane has been distilled off, 18 g of product remain. Purity 94% according to GC analysis.

Example A7

2-Chloro-3,5,6-trifluoro-4-nitrophenol

Analogously to Example A5, nitration of 28 g of 2-chloro-3,5,6-trifluorophenol gives 25 g of 2-chloro-3,5,6-trifluoro-4-nitrophenol, having a purity of 93% and a melting point of 107°–109° C.

Example A8

2,6-Dichloro-3,5-difluoro-4-amino-phenol 18 g of 2,6-dichloro-3,5-difluoro-4-nitrophenol are hydrogenated in 100 ml of methanol in the presence of 1.5 g of Raney nickel at 25°–45° C. and 30–50 bar of hydrogen until hydrogen is no longer taken up. The mixture is filtered, and the solution is then freed from the solvent under reduced pressure. 13 g of aminophenol remain (GC purity 98.4%); m.p. 151° C.

Example A9

2-Chloro-3,5,6-trifluoro-4-amino-phenol

Analogously to Example A7, hydrogenation of 25 g of 2-chloro-3,5,6-trifluoro-4-nitro-phenol in 120 ml of methanol and 2 g of Raney nickel gives 20 g of aminophenol (GC purity 97%).

Analogously to Example A1, the following compounds of the formula (IVA) are obtained.

(IVa)

[Structure: X'-C(=O)-NH-phenyl ring with Y¹, Hal, OH, Y², Y³ substituents]

| Ex. No. | X' | Y¹ | Y² | Y³ | Hal |
|---------|----|----|----|----|-----|
| A11 | 4-methylcyclohex-1-enyl | Cl | H | H | Cl |
| A12 | 4-methylcyclohex-2-enyl | Cl | H | Cl | H |
| A13 | 3,4-dimethylcyclohex-2-enyl | Cl | H | H | Cl |
| A14 | 3,4-dimethylcyclohex-2-enyl | Cl | H | Cl | H |
| A15 | 3,4,5-trimethylcyclohex-3-enyl | Cl | H | Cl | H |
| A16 | 3,4,5-trimethylcyclohex-3-enyl | Cl | H | H | Cl |

Example

Botrytis test (bean)/protective
Solvent: 4.7 parts by weight of acetone
Emulsifier: 0.3 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small pieces of agar covered with Botrytis cinerea are placed on each leaf. The inoculated plants are placed in a darkened humid chamber at 20° C. 3 days after the inoculation, the size of the infected spots on the leaves is evaluated.

In this test, a clearly high activity is shown, for example, by the compounds of the following Preparation Examples: 1, 2, 3, 4, 6, 7, 8, 9, 35 and 42.

It is understood that the specification and examples are illustrative but not limitative of the present invention and that other embodiments within the spirit and scope of the invention will suggest themselves to those skilled in the art.

We claim:

1. A cycloalkyl or cycloalkenyl-carboxanilide of the formula

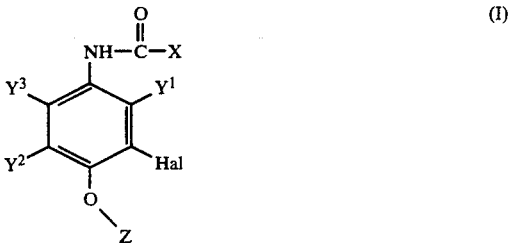

(I)

in which
X represents optionally alkyl-substituted cycloalkyl or optionally alkyl-substituted cycloalkenyl,
Hal represents halogen, and
$Y^1$, $Y^2$ and $Y^3$ independently of one another represent hydrogen, halogen, optionally halogen-substituted alkyl, optionally halogen-substituted alkoxy or optionally halogen-substituted alkylthio, and
Z represents the group $COR^1$, where
$R^1$ represents optionally halogen-substituted alkyl, alkenyl, alkoxyalkyl, alkylthioalkyl, polyalkoxyalkyl and optionally substituted cycloalkyl, optionally substituted phenyl, optionally substituted phenylalkyl or substituted phenoxyalkyl.

2. A compound according to claim 1, in which
X represents cyclopropyl, cyclobutyl, cyclopentyl, cyclohexyl or cycloheptyl, each of which is optionally monosubstituted to tetrasubstituted by identical or different substituents from the group consisting of straight-chain or branched alkyl radicals having 1–4 carbon atoms, or represents cycloalkenyl having 5–7 ring members and optionally monosubstituted to hexasubstituted by identical or different substituents from the group consisting of straight-chain and branched alkyl radicals having 1–4 carbon atoms,
Hal represents fluorine, chlorine or bromine,
$Y^1$, $Y^2$ and $Y^3$ are identical or different and represent hydrogen, fluorine, chlorine, bromine, straight-chain or branched alkyl having 1–4 carbon atoms, straight-chain or branched alkoxy or alkylthio each having 1–4 carbon atoms, or represent halogenoalkyl, halogenoalkoxy or halogenoalkylthio each having 1–4 carbon atoms in the straight-chain or branched alkyl moiety and having 1–5 identical or different halogen atoms,
Z represents $COR^1$, where
$R^1$ represents $C_1$-$C_8$-alkyl, $C_2$-$C_8$-alkenyl, $C_1$-$C_4$-alkoxy-$C_1$-$C_4$-alkyl, $C_1$-$C_4$-alkoxy-$C_1$-$C_4$-alkoxy-$C_1$-$C_4$-alkyl or $C_1$-$C_4$-alkylthio-$C_1$-$C_4$-alkyl, each of which is optionally monosubstituted to nonasubstituted by halogen, or represent $C_3$-$C_7$-cycloalkyl which is unsubstituted or monosubstituted to pentasubstituted by identical or different substituents from the group consisting of $C_1$-$C_4$-halogenoalkyl, halogen, $C_1$-$C_4$-alkyl, $C_1$-$C_4$-alkoxy, hydroxyl and $C_1$-$C_6$-alkylcarbonyloxy, or represent phenyl-$C_1$-$C_4$-alkyl which is unsubstituted or monosubstituted to pentasubstituted in the phenyl moiety by identical or different substituents from the group consisting of $Y^{1'}$-$Y^{5'}$, or represent phenoxyalkyl which is unsubstituted or monosubstituted to pentasubstituted in the phenyl moiety by identical or different substituents from the group consisting of $Y^{1'}$-$Y^{5'}$, where $Y^{1'}$-$Y^{5'}$ have the meaning of $Y^1$-$Y^3$, $NO_2$ and cyano.

3. A compound according to claim 1, in which

X represents cyclopropyl, cyclobutyl, cyclopentyl, cyclohexyl or cycloheptyl, each of which is monosubstituted or disubstituted by identical or different substituents from the group consisting of straight-chain or branched alkyl radicals having 1–4 carbon atoms, or represents cyclopentenyl, cyclohexenyl or cycloheptenyl, each of which is optionally monosubstituted or disubstituted by identical or different substituents from the group consisting of straight-chain and branched alkyl radicals having 1–4 carbon atoms, $Y^1$, $Y^2$ and $Y^3$ identical or different and represent hydrogen, fluorine, chlorine, bromine, methyl or trifluoromethyl, and Hal represents fluorine, chlorine or bromine, Z represents $COR^1$, where $R_1$ represents $C_1$-$C_6$-alkyl, $C_2$-$C_6$-alkenyl, $C_1$-$C_4$-alkoxy-$C_1$-$C_4$-alkyl, $C_1$-$C_4$-alkoxy-$C_1$-$C_4$-alkoxy-$C_1$-$C_4$-alkyl or $C_1$-$C_4$-alkylthio-$C_1$-$C_2$-alkyl, or represent $C_3$-$C_7$-cycloalkyl which is unsubstituted or monosubstituted to trisubstituted by identical or different substituents from the group consisting of fluorine, chlorine, bromine, $C_1$-$C_2$-alkyl, $C_1$-$C_2$-alkoxy and $C_1$-$C_6$-alkylcarbonyloxy, or represent phenyl which is unsubstituted or monosubstituted to trisubstituted by identical or different substituents from the group consisting of nitro, cyano, fluorine, chlorine, bromine, methyl, trifluoromethyl, trifluoromethylthio, methoxy and trifluoromethoxy, or represent phenyl-$C_1$-$C_2$-alkyl which is unsubstituted or monosubstituted to trisubstituted by identical or different substituents from the group consisting of nitro, cyano, fluorine, chlorine, bromine, methyl, trifluoromethyl, trifluoromethylthio, methoxy and trifluoromethoxy, or represent phenoxy-$C_1$-$C_2$-alkyl which is unsubstituted or monosubstituted to trisubstituted by identical or different substituents from the group consisting of nitro, cyano, fluorine, chlorine, bromine, methyl, trifluoromethyl, trifluoromethylthio, methoxy and trifluoromethoxy.

4. A compound according to claim 1, in which

X represents cyclopentyl, cyclohexyl, cycloheptyl, cyclopentenyl, cyclohexenyl or cycloheptenyl, each of which is substituted in the 1- or 1,3-position by methyl or ethyl and each of which is optionally additionally substituted by a further alkyl radical having 1-3 carbon atoms, Hal represents fluorine, chlorine or bromine, and $Y^1$, $Y^2$ and $Y^3$ are identical or different and represent hydrogen, fluorine, chlorine, bromine or trifluoromethyl, Z represents $COR^1$, where $R^1$ represents $C_1$-$C_4$-alkyl, $C_2$-$C_5$-alkenyl, $C_1$-$C_4$-alkoxy-$C_1$-$C_4$-alkyl or $C_1$-$C_4$-alkoxy-$C_1$-$C_4$-alkoxy-$C_1$-$C_4$-alkyl, or represent $C_3$-$C_7$-cycloalkyl which is monosubstituted to trisubstituted by identical or different substituents from the group consisting of methoxy, fluorine, chlorine, bromine, methyl and $C_1$-$C_4$-alkylcarbonyloxy, or represent phenyl which is monosubstituted to trisubstituted by identical or different substituents from the group consisting of nitro, cyano, fluorine, chlorine, bromine, methyl and methoxy, or represents phenylmethyl which is monosubstituted to trisubstituted by identical or different substituents from the group consisting of nitro, cyano, fluorine, chlorine, bromine, methyl and methoxy.

5. A fungicidal composition comprising a fungicidally effective amount of a compound according to claim 1 and a diluent.

6. A method of combating fungi which comprises applying to such fungi or to a locus from which it is desired to exclude such fungi a fungicidally effective amount of a compound according to claim 1.

7. An acylaminophenol of the formula

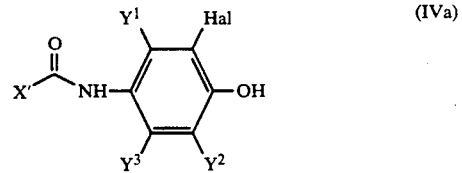

(IVa)

in which

X' represents an optionally alkyl-substituted cycloalkenyl radical, preferably a $C_1$-$C_2$-alkyl-substituted cyclopentenyl radical, cyclohexenyl radical or cycloheptenyl radical, and Hal represents halogen, and $Y^1$, $Y^2$ and $Y^3$ independently of one another represent hydrogen, halogen, optionally halogen-substituted alkyl, optionally halogen-substituted alkoxy or optionally halogen-substituted alkylthio.

* * * * *